US006384016B1

(12) United States Patent
Kaarsholm (10) Patent No.: US 6,384,016 B1
(45) Date of Patent: May 7, 2002

(54) STABILIZED AQUEOUS PEPTIDE SOLUTIONS

(75) Inventor: Niels C. Kaarsholm, Vanløse (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/265,141

(22) Filed: Mar. 8, 1999

Related U.S. Application Data
(60) Provisional application No. 60/078,422, filed on Mar. 18, 1998.

(30) Foreign Application Priority Data

Mar. 13, 1998 (EP) .............................. 98610006

(51) Int. Cl.$^7$ .......................... A61K 38/00; A61K 38/26
(52) U.S. Cl. .......................... 514/12; 514/866; 530/303; 530/308; 530/324
(58) Field of Search .................. 514/12, 866; 530/324, 530/303, 308

(56) References Cited

U.S. PATENT DOCUMENTS

| 5,120,712 A | | 6/1992 | Habener ....................... 514/12 |
| 5,652,216 A | * | 7/1997 | Kornfelt et al. ............... 514/12 |
| 5,707,641 A | * | 1/1998 | Gertner et al. .............. 424/422 |

FOREIGN PATENT DOCUMENTS

| EP | 0 619 322 A2 | | 10/1994 |
| GB | 1 202 607 | * | 8/1970 |
| WO | WO 95/32730 | | 12/1995 |

OTHER PUBLICATIONS

Schneider et al., *The Journal of Biological Chemistry*, vol. 247, No. 16, pp. 4986–4995, 1972.*

W.B. Gratzer et al., "Relation Between Conformation and Association State" The Journal of Biological Chemistry, 244, No. 24, Dec. 25, 1969, pp. 6675–6679.

Sasaki et al., "X–Ray Analysis of Glucagon and Its Relationship to Receptor Binding", Nature Vo. 257, Oct. 30, 1975, pp. 751–757.

Wagman et al., "Proton NMR Studies of The Association And Folding of Glucagon In Solution", Elsevier/North–Holland Biomedical Press, vol. 119, No. 2, Oct. 1980, pp. 265–270.

Epand et al., "Molecular Interactions In The Model Lipoprotein Complex Formed Between Glucagon and Dimyristoylglycerophosphocholine", Biochemistry vol. 16, No. 20, 1977.

Schneider et al., "Polypeptide Hormone Interaction" (Glucagon Binding To Lysolecithin), The Journal of Biological Chemistry, Vo. 247, No. 16, Aug. 15, 1972, pp. 4986–4991.

Schneider et al., "Polypeptide Hormone Interaction" (Conformational Changes of Glucagon Bound To Lysolecithin), The Journal of Biological Chemistry, Vo., 247, No. 16, Aug. 25, 1972, pp. 4992–4995.

Robinson et al., "Lipid–Induced Conformational Changes in Glucagon, Secretin, and Vasoactive Intestinal Peptide", Biopolymers, vol. 21, 1982, pp. 1217–1228.

Hamed et al., "Bahavior of Amphipathic Helices on Analysis Via Matrix Methods, With Application to Glucagon, Secretin, and Vasoactive Intestinal Peptide", Biopolymers, vol. 22, 1983, pp. 1003–1021.

Wu et al., "Helical Conformation of Glucagon in Surfactant Solutions", Americal Chemical Society, 1980, pp. 2117–2122.

Bösch et al., "Physiocochemical Characterization of Glucagon–Containing Lipid Micelles" Biochimic et Biophysica Acta, 603 (1980) pp. 298–312.

Thornton et al., Structure of Glucagon–Like Peptide (7–36) Amide in a Dodecylphosphocholine Micelle as Determined by 2D NMR, Biochemistry 1994, 33, pp. 3532–3539.

* cited by examiner

*Primary Examiner*—Christopher S. F. Low
*Assistant Examiner*—Abdel A. Mohamed
(74) *Attorney, Agent, or Firm*—Reza Green, Esq.; Valeta A. Gregg, Esq.

(57) ABSTRACT

Aqueous compositions comprising at least one peptide selected from glucagon, GLP-1, and analogues and derivatives thereof together with a stabilizing and solubilizing amount of at least one detergent, said detergent having at least 2 positive charges, at least 2 negative charges, or a combination of at least one positive charge and at least one negative charge.

9 Claims, 7 Drawing Sheets

SEQUENCE LISTING

```
<160> NUMBER OF SEQ ID NOS:  1

<210> SEQ ID NO 1
<211> LENGTH: 31
<212> TYPE: PRT
<213> ORGANISM: Human
<220> FEATURE:
<221> NAME/KEY: VARIATION
<222> LOCATION: (0)...(0)
<223> OTHER INFORMATION: Xaa at position 31 is any amino acid

<400> SEQUENCE: 1

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Xaa
             20                  25                  30
```

STABILIZED AQUEOUS PEPTIDE SOLUTIONS

CROSS-REFERENCE TO RELATED APPLICATIONS

This application claims priority under 35 U.S.C. 119 of EP application EP 98610006.3 filed Mar. 13, 1998 and U.S. provisional application 60/078,422 filed Mar. 18, 1998, the contents of which are fully incorporated herein by reference.

FIELD OF THE INVENTION

The present invention relates to stable, injectable aqueous solutions of peptides such as glucagon, glucagon-like peptide-1 (GLP-1, e.g. GLP-1(7–37) and GLP-1(7–36) amide) and analogues and derivatives thereof.

BACKGROUND OF THE INVENTION

Glucagon and glucagon-like peptide 1 (GLP-1) are polypeptide hormones both derived from proglucagon. Upon tissue-specific processing, glucagon is produced in the pancreas, while GLP-1 is predominantly secreted in the intestine. Physiologically, both peptides play major roles in the regulation of blood glucose. Glucagon is directly involved via glycogenolytic as well as gluconeogenetic effects. GLP-1 is indirectly involved via stimulation of insulin and inhibition of glucagon secretion. Thus, the two peptides affect the blood glucose in opposite directions.

Due to its glycogenolytic effect on the liver, glucagon is used for the treatment of acute hypoglycemia (e.g. "insulin shock"). In addition, glucagon excerts a spasmolytic effect on smooth muscles, and this effect is used clinically in connection with several imaging procedures, especially radiology.

GLP-1 fragments such as GLP-1 (7–37), GLP-1 (7–36) amide and functional analogues thereof (hereinafter designated GLP-1 compounds) stimulate pancreatic insulin release in the presence of glucose, and this finding suggests that GLP-1 compounds may be useful in the treatment of type II diabetes.

Glucagon (29 amino acids; see e.g. *The Merck Index*, 10$^{th}$ Edition for the amino acid sequence) and GLP-1 compounds (typically about 29–31 amino acids) are single chain highly homologous peptides. While little information is available on the solution behaviour of GLP-1 compounds, the physico-chemical properties of glucagon are well described in the literature (J.Biol.Chem. 244, 6675–6679 (1969); Nature 257, 751–757 (1975); FEBS Letts. 119, 265–270 (1980)). The peptide exhibits very low solubility in water at a pH in the range of about 4–9. Outside this region, aqueous solutions are generally metastable and prone to gel formation or flocculation within hours of their preparation.

Accordingly, glucagon compositions for injection are currently marketed in the form of a lyophilized powder which is to be reconstituted using a suitable diluent shortly before use. The resulting acidic solution may then be injected. In contrast with the single-dose compositions of glucagon used for acute hypoglycemia and the motility indication in radiology, the utility of GLP-1 compounds for the treatment of type II diabetes generally involves multiple-dose soluble compositions. Given the instability of glucagon, the formulation of such compositions is inherently difficult.

Thus, there is a need for stable aqueous formulations of peptides such as glucagon and GLP-1 compounds. In the case of glucagon, the availability of a ready-to-use composition is desirable for emergency treatment of acute hypoglycemia, enabling the patient or another person present to treat the hypoglycemic incidence immediately. Also for the mobility indication for glucagon used in radiology, and for the type II diabetes indication for GLP-1 compounds, the availability of a ready-to-use aqueous composition provides obvious advantages in terms of convenience and safety.

Glucagon compositions solubilized by the addition of detergent have received relatively little attention in the literature. British patent No. 1 202 607 describes the use of either cationic (quarternary ammonium bases) or anionic (alkyl-aryl-sulphonates), monovalent detergents. These compounds provide enhanced solubilization of 1 mg/ml glucagon over a limited pH range using a 6-fold molar excess of detergent.

A series of other studies on glucagon-detergent interactions employ much lower glucagon concentrations and do not address the effect of detergent on peptide solubility. Thus, in studies using 0–200 μM of the amphoteric (twitterionic) detergent hen egg lysolecithin, binding of detergent was shown to induce partial helical structure in solutions of glucagon containing about 0.02 mg/ml peptide (J.Biol.Chem. 247, 4986–4991; 4992–4995; (1972)). Similarly, in studies employing dilute (0.005–0.05 mg/ml) solutions of glucagon, lysolecithin was found more efficient than the anionic detergents dipalmitoyl phosphatidic acid and sodium dodecyl sulfate (SDS) in inducing partial helical structure in glucagon (Biopolymers 21, 1217–1228 (1982); Biopolymers 22, 1003–1021 (1983)).

At the other extreme, a few examples are available characterizing the interaction between glucagon and concentrated detergent solutions. These include the binding of dilute glucagon to micelles of the anionic detergent SDS at 25 mM, pH 2 (Biochemistry 19, 2117–2122, (1980)), and the solubilization of glucagon (up to 20 mg/ml) via binding to micelles of the amphoteric dodecylphosphocholine present in a 40-fold molar excess (e.g. 3.5 mg/ml glucagon is solubilized using 40 mM detergent at neutral pH; Biochim.Biophys.Acta 603, 298–312, (1980))

With the exception of a single example describing the solubilization of 20 mg/ml GLP-1 (7–36) amide bound to micelles of dodecylphosphocholine at 280 mM (cf. the glucagon case above, Biochemistry 33, 3532–3539, 1994), no reports are available on the binding of detergents by GLP-1 compounds and the resulting effect on peptide solubility and stability. In contrast, several ways of preparing prolonged delivery of GLP-1 compounds have been described (e.g. European patent application No. 0619322 and column 6 of U.S. Pat. No. 5,120,712). The possibilities include use of polymers, incorporation into particles of polymer material or into an oil suspension, addition of zinc ion, protamine sulphate and/or phenolic compounds, and preparation of amorphous/crystalline formulations.

BRIEF DESCRIPTION OF THE INVENTION

It has now surprisingly been found that soluble and stable formulations of glucagon and GLP-1 compounds may be prepared by means of addition of detergents carrying multiple charges (i.e. two or more negative, two or more positive, or both positive and negative charges). When added in an amount corresponding to e.g. about 0.5–20 moles of detergent per mole of peptide, this class of detergents is capable of solubilizing pharmaceutically relevant concentrations of glucagon and GLP-1 compounds in the entire pH range from 4 to 9. The expanded pH range allows optimal selection of conditions to suppress chemical degradation of the solubilized peptide. Furthermore, preferred detergents The amino acid sequence of GLP-1 (7–36)amide and GLP-1 (7–37) is as given in the general formula (I) below:

$$\begin{array}{c}\text{7 8 9 10 11 12 13 14 15 16 17 18 19 20 21 22 23 24 25 26 27 28 29 30 31 32 33 34 35 36}\\ \text{His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-X}\\ \text{(SEQ ID NO: 1)}\end{array} \tag{I}$$

consist of naturally occurring building blocks which are more biologically acceptable than those previously described.

Thus, in its broadest aspect, the present invention relates to a pharmaceutical composition in the form of a solution comprising a polypeptide containing an amphiphatic α-helix which is stabilized by interaction with a detergent carrying multiple charges. Such polypeptides include, but are not limited to, glucagon, GLP-1 compounds, corticotropin (ACTH), calcitonin, and functional analogues thereof.

One aspect of the invention relates to an aqueous composition in the form of a solution comprising at least one peptide selected from glucagon, GLP-1, and analogues and derivatives thereof together with a stabilizing and solubilizing amount of at least one detergent, said detergent having at least 2 positive charges, at least 2 negative charges, or a combination of at least one positive charge and at least one negative charge, the peptide or analogue or derivative thereof being present in a concentration of at least about 0.1 mg/ml, with the proviso that the detergent is not dodecyl phosphocholine.

Another aspect of the invention relates to a method for stabilizing an aqueous composition in the form of a solution comprising at least one peptide selected from glucagon, GLP-1 and analogues and derivatives thereof by adding to the composition a stabilizing and solubilizing amount of at least one such detergent having multiple charges.

In a further embodiment, the invention relates to a method for treating insulin dependent or non-insulin dependent diabetes mellitus or obesity in a patient in need of such treatment, comprising administering to the patient a therapeutically effective amount of an appropriate stabilized aqueous composition as described herein.

DETAILED DESCRIPTION OF THE INVENTION

Glucagon and GLP-1 compounds belong to a class of polypeptides which have the potential of forming amphiphatic helices, i.e., one face of the helical structure displays mainly hydrophobic amino acid side chains, while the other face exposes hydrophilic and/or charged side chains. In polypeptides of this type, the formation of the amphiphatic helical structure is often linked to inter-peptide helix self-association along the interfaces defined by the hydrophobic patches.

A simple system is used to describe fragments and analogues of GLP-1. Thus, for example, Gly$^8$-GLP-1 (7–37) designates a fragment of GLP-1 formally derived from GLP-1 by deleting the amino acid residues Nos. 1 to 6 and substituting the naturally occurring amino acid residue in position 8 (Ala) by Gly. Similarly, Lys$^{34}$(N$^\epsilon$-tetradecanoyl)-GLP-1 (7–37) designates GLP-1 (7–37) wherein the &-amino group of the Lys residue in position 34 has been tetradecanoylated.

which shows GLP-1 (7–36)amide when X is NH$_2$ and GLP-1 (7–37) when X is Gly-OH.

In the present text, the designation "analogue" is used to designate a peptide wherein one or more amino acid residues of the basic GLP-1 peptide have been substituted by another amino acid residue and/or wherein one or more amino acid residues of the peptide have been deleted and/or wherein one or more amino acid residues have been added to the peptide. Such addition can take place either at the N-terminal end or at the C-terminal end or both. The term "derivative" is used in the present text to designate a peptide in which one or more of the amino acid residues of the peptide have been chemically modified, e.g. by alkylation, acylation, ester formation or amide formation. For the sake of simplicity, the term "peptide" will generally be used herein to refer to the glucagon and GLP-1 peptides as such as well as analogues and derivatives thereof.

The present invention is based on situations where the hydrophilic patch of the putative amphiphatic helix displays two or more charges. By the addition of a detergent carrying a complementary set of multiple charges, a stabilizing and solubilizing helix-forming effect will result from a combination of two factors, i.e. 1) charge—charge interactions between the polar head of the detergent and the charged amino acid side chains of the helix; and 2) the hydrophobic tail of the detergent serving as a template for association with the hydrophobic patch of the same or that of a neighboring helix.

The stabilized solutions of the invention can be used for parenteral, pulmonal or nasal administration. Such solutions remain stable and retain biological activity when stored at temperatures of e.g. 4°–25° C. for extended periods of time.

Suitable detergents according to the invention are characterized by having multiple charges, i.e. two or more positive charges, two or more negative charges, or a combination of at least one positive charge and at least one negative charge. The advantage of multiple charges as opposed to monovalent ionic detergents is illustrated in the appended FIG. 1. This figure compares the pH-dependence of the equilibrium solubility in 1 mg/ml solutions of glucagon in the absence of additives and in the presence of 1 mM of each of the following detergents: a) cetyltrimethylammonium bromide (CTAB, i.e. monovalent cationic), b) sodium dodecyl sulfate (SDS, i.e. monovalent anionic) and c) myristoyl lysophosphatidylcholine (LPCM, i.e. amphoteric).

Figure 1:
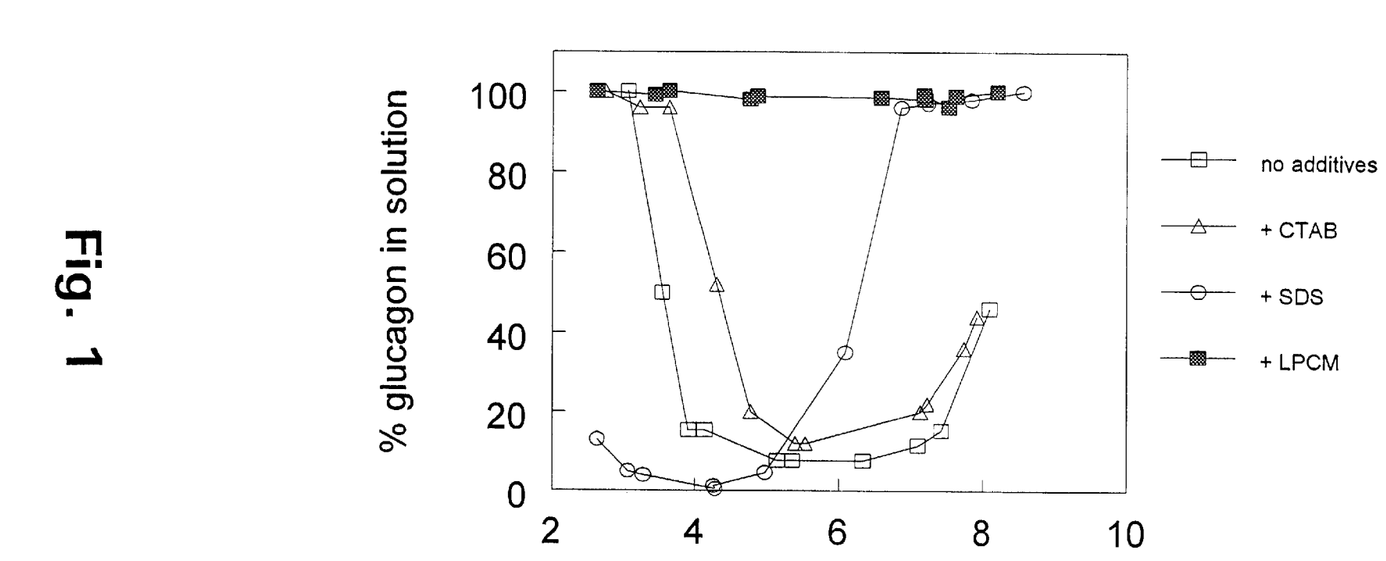

These data show that, while the monovalent cationic and anionic detergents promote solubility at the acidic and basic limbs of the solubility curve, respectively, the amphoteric detergent effects full solubility over the entire pH range. Furthermore, the effect of the amphoteric detergent is clearly much stronger than that expected from the sum of the effects seem with each of the monovalent detergents.

The detergents used in accordance with the present invention contain a polar head group with two or more charges and one or more aliphatic side chains each having at least 6 carbon atoms. In the preferred detergents, any aliphatic side chains have 8–20, e.g. 10–18 carbon atoms. With respect to the polar head group, useful detergents include those selected from the group consisting of lysophospholipids (e.g. 1-acyl-sn-glycero-3-phosphate esters of ethanolamine, choline, serine or threonine). Lauroyl and myristoyl derivatives of lysophosphatidylcholine, lysophosphatidylserine and lysophosphatidylthreonine are particularly useful. Alternatively, the polar group may be a basic amino acid (e.g. $N^{\alpha}$-acylated derivatives of lysine, arginine or histidine, or side-chain acylated derivatives of lysine or arginine). It may also be a dipeptide (e.g. $N^{\alpha}$-acylated derivatives of dipeptides comprising any combination of lysine, arginine or histidine and a neutral or acidic amino acid) or a tripeptide (e.g. an $N^{\alpha}$-acylated derivative of a tripeptide comprising any combination of a neutral amino acid and two charged amino acids). The polar head group may also be selected from the group of betaines, i.e. amphoteric compounds where the basic group is quarternary ammonium, sulfonium or phosphonium and the acidic group is carboxylate, carboxyalkyl, sulfonate or propanesulfonate. Finally, the detergent may be selected from, the group of imidazoline derivatives. It is preferred, however, that the detergent is not dodecyl phosphocholine.

An example of a suitable composition according to the invention is one comprising about 0.5–2.5 mg of peptide per ml, e.g. about 1 mg of peptide per ml, and about 1–3 mM, e.g. about 2 mM of the detergent, e.g. lauroyl or myristoyl lysophosphatidylcholine.

The stable aqueous, injectable solutions of glucagon and GLP-1 compounds according to the invention may be prepared by bringing together the peptide, water and a stabilizing and solubilizing amount of detergent. Typically, the solutions will contain other excipients to adjust ionic strength and provide buffering capacity and antibacterial action as needed. The final peptide concentration will be at least about 0.1 mg/ml, typically about 0.2–5 mg/ml, e.g. about 0.5–3 mg/ml, and the detergent is typically employed in an amount corresponding to at least about 0.3 mole of detergent per mole of peptide, more typically at least about 0.5 mole detergent/mole of peptide and up to about 40 moles detergent/mole of peptide, typically up to about 30 moles detergent/mole peptide, e.g. about 1–20 moles detergent/mole peptide, such as about 1–10 moles detergent/mole peptide. For a given peptide and detergent and a given concentration of peptide, a person skilled in the art will readily be able to determine a suitable detergent concentration that results in the desired stabilization. Isotonic ionic strength may be provided by conventional pharmaceutically acceptable agents such as NaCl, glycerol or mannitol. pH is buffered in the desired range between about 4 and about 8, typically by using acetate, citrate or phosphate buffers at 1–10 mM concentration as is well-known in the art. Finally, when a preservative is needed, appropriate antibacterial action is secured by the addition of, typically, phenol, m-cresol or benzyl alcohol or mixtures thereof.

The compositions of the invention can be used in the treatment of various diseases that can be treated by administering glucagon, GLP-1, or analogues or derivatives thereof. The particular peptide to be used and the optimal dose level for any patient will depend on the disease to be treated and on a variety of factors, including the efficacy of the specific peptide employed, the age, body weight, physical activity, and diet of the patient, on a possible combination with other drugs, and on the severity of the case. A typical dose of GLP-1 for regulation of the blood sugar level may e.g. be about 0.5–1 mg, for example once a day. A typical dose for glucagon may be approximately 1 mg, e.g. for gastro-intestinal imaging. It is recommended that the dosage of the active compound in question be determined for each individual patient in each case by those skilled in the art.

The invention will be further illustrated by the following non-limiting examples.

EXAMPLES

Materials & Methods
EQUILIBRIUM SOLUBILITY

For pH-solubility profiles, solutions containing the peptide and additives (detergent and, where indicated, other excipients) at the appropriate concentrations were prepared at pH 9–10. The solutions were filtered, samples were withdrawn, and the pH was adjusted to the desired value in the range of 3–8. The samples were left for 24 hours at 23° C. to attain solubility equilibrium. After centrifugation (20,000 g for 20 minutes, 23° C.) of each sample, the pH was measured, and the solubility was determined from measurement of the absorbance at 276 nm of the supernatant.

Long Term Physical Stability

Glucagon and GLP-1 (7–37) were dissolved at twice the desired final concentration and incubated briefly (<10 minutes) at pH 11.5, 23° C. before filtration and mixing with an equal volume of a filtered solution containing all the excipients in twice the desired final concentration. The pH was then measured and adjusted as needed. The solution was transferred to pen-fill cartridges containing a small glass ball (to allow visual determination of changes in solution viscosity). The containers were sealed and incubated at the desired temperature between 4° C. and 37° C. At appropriate time intervals, the samples were gently turned and visually examined using a light box. When physical changes were apparent (precipitation, crystallization or gelation), the sample was centrifuged and the absorbance was measured in the supernatant to determine whether the component coming out of solution was the peptide or not.

Example 1

Figure 2:
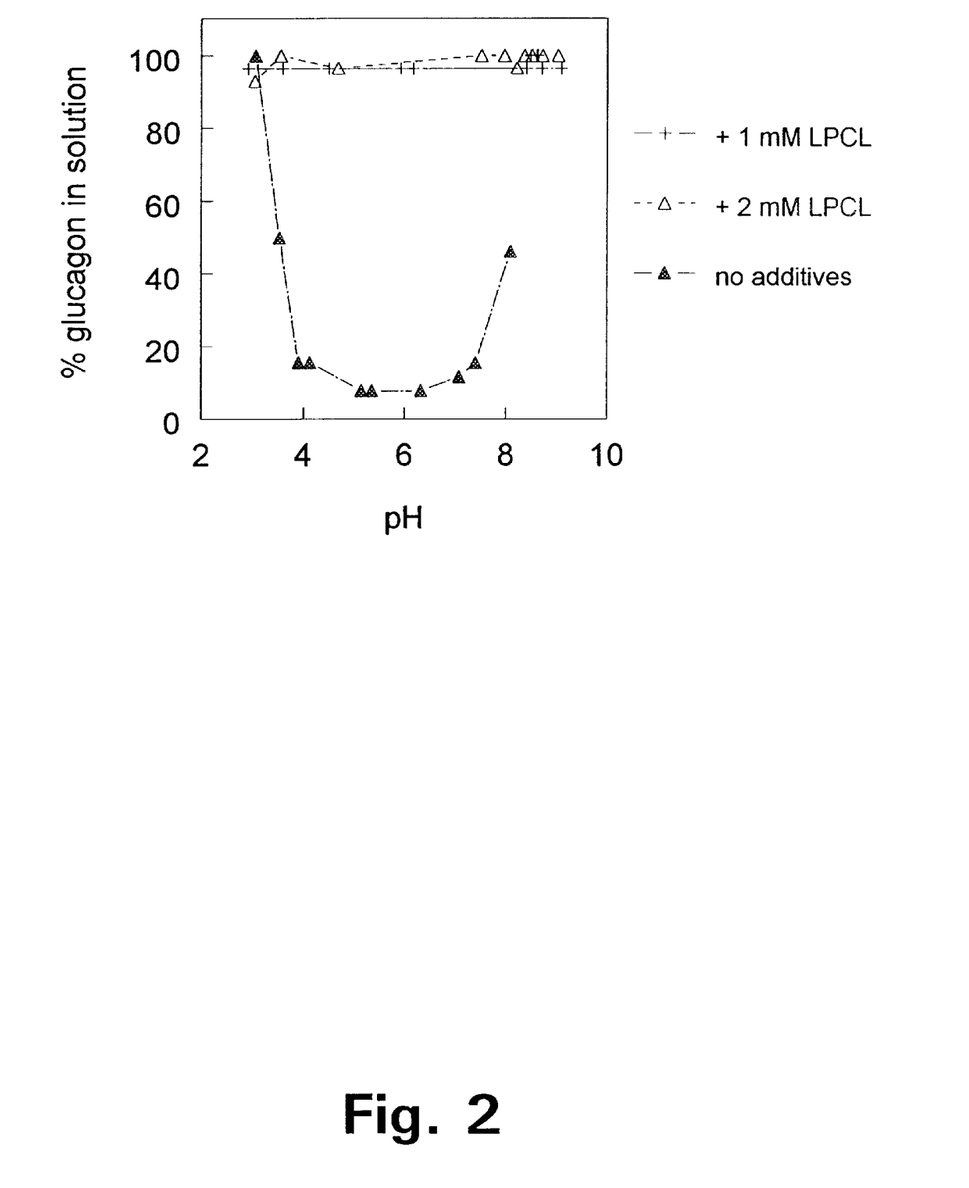

Equilibrium solubility was determined as a function of pH for 1 mg/ml glucagon solutions in the absence of additives and in the presence of 1 or 2 mM of the detergent LPCL (lauroyl lysophosphatidylcholine). The results are shown in FIG. 2. It may be seen that excellent results, i.e. approximately 100% solubility throughout the pH range tested, were obtained with both concentrations of LPCL. For the control solution without additives, acceptable solubility was only obtained at pH 3.

Example 2

Figure 3:
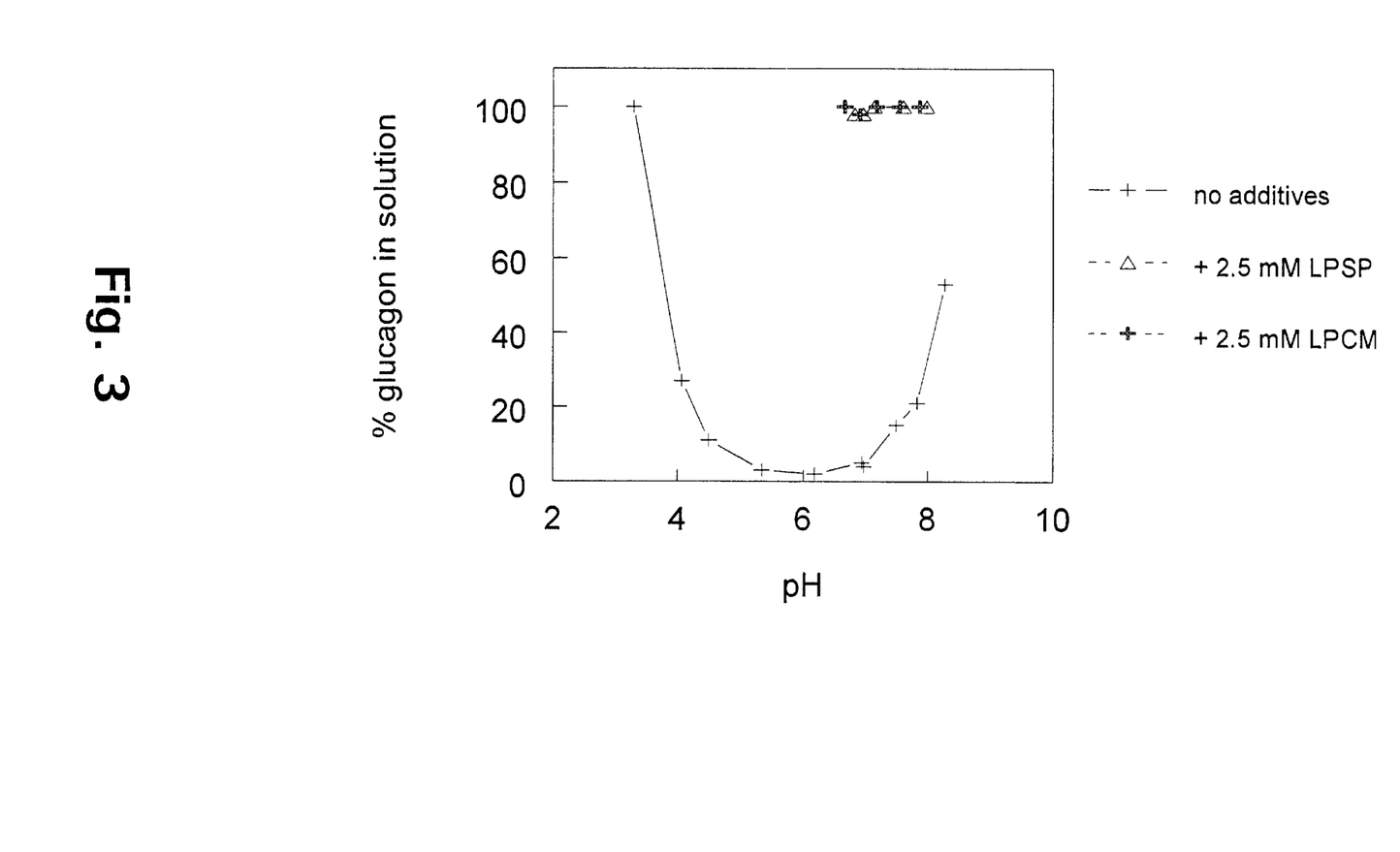

Equilibrium solubility was determined as a function of pH in the pH range of 6–8 for 2 mg/ml solutions of glucagon in the absence of additives and in the presence of 2.5 mM of the detergents LPSP (palmitoyl lysophosphatidyl-L-serine) and LPCM (myristoyl lysophosphatidyl choline). The results are shown in FIG. 3. Both additives provided 100% solubility within the tested pH range of 6–8.

Example 3

Figure 4:
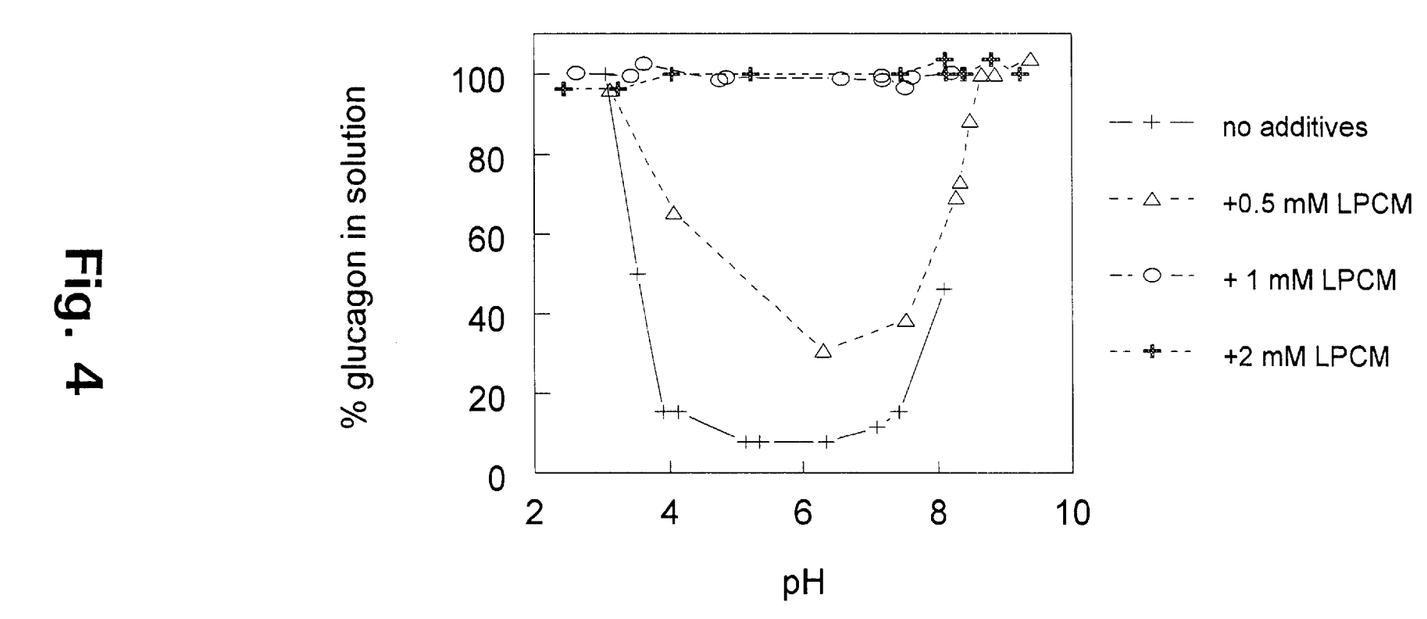

Equilibrium solubility was determined as a function of pH for 1 mg/ml solutions of glucagon in the absence of additives and in the presence of increasing amounts of LPCM (myristoyl lysophosphatidyl choline). The results are shown in FIG. 4. For solutions containing 1 or 2 mM LPCM, approximately 100% solubility was obtained throughout the entire pH range, while 0.5 mM LCPM provided insufficient solubility at pH 4–8. However, even the addition of 0.5 mM LCPM gave a substantial improvement over the control solution.

Example 4

The following examples illustrate various glucagon solutions prepared according to the invention. All of the indicated solutions remained clear, i.e. the glucagon remained completely soluble, for at least the duration of the observation period of four weeks:

| mg/ml Glucagon | mM detergent | buffer, pH | Other additive | Temperature |
|---|---|---|---|---|
| 2 | 5.0 LPCM | 5 mM phosphate, 7.2 | | 4° C. |
| 2 | 5.0 LPCM | 5 mM phosphate, 7.2 | 0.2 M mannitol | 4° C. |
| 1 | 5.0 LPCM | 5 mM phosphate, 6.0 | 0.12 M NaCl | 4° C. |
| 1 | 5.0 LPCM | 5 mM phosphate, 6.5 | 0.2 M mannitol | 4° C. |
| 1 | 2.0 LPCM | 5 mM phosphate, 7.2 | | 4° C. |
| 1 | 2.0 LPCM | 5 mM phosphate, 7.2 | | 4° C. |
| 1 | 2.0 LPCM | 5 mM phosphate, 6.0 | 0.12 M NaCl | 4° C. |
| 0.5 | 1.0 LPCM | 5 mM phosphate, 7.2 | 0.12 M NaCl | 4° C. |
| 0.5 | 2.0 LPCM | 5 mM phosphate, 7.2 | 0.12 M NaCl | 4° C. |
| 0.5 | 2.0 LPCM | 5 mM acetate, 4.5 | 0.12 M NaCl | 4° C. |
| 0.5 | 2.0 LPCM | 5 mM acetate, 4.5 | 0.12 M NaCl | 25° C. |
| 1 | 2.5 HPS | 5 mM phosphate, 7.2 | 0.2 M mannitol | 4° C. |
| 1 | 5.0 LPCL | 5 mM phosphate, 7.0 | 0.12 M NaCl | 4° C. |
| 1 | 5.0 LPCL | 5 mM phosphate, 6.0 | 0.12 M NaCl | 4° C. |
| 1 | 2.5 LPCL | 5 mM phosphate, 7.2 | 0.2 M mannitol | 4° C. |
| 0.5 | 2.0 LPCL | 5 mM phosphate, 7.2 | 0.2 M mannitol | 4° C. |
| 0.5 | 2.0 LPCL | 5 mM phosphate, 7.2 | 0.12 M NaCl | 4° C. |
| 0.5 | 2.0 LPCL | 5 mM acetate, 5.0 | 0.2 M mannitol | 4° C. |
| 0.5 | 2.0 LPCL | 5 mM acetate, 5.0 | 0.2 M mannitol | 25° C. |
| 0.5 | 2.0 HPS | 5 mM acetate, 4.5 | 0.12 M NaCl | 25° C. |

LPCM = myristoyl lysophosphatidylcholine
HPS = N-Hexadecyl-N,N-dimethyl-3-ammonio-1-propanesulfonate
LPCL = Lauroyl lysophosphatidylcholine

Example 5

Figure 5:
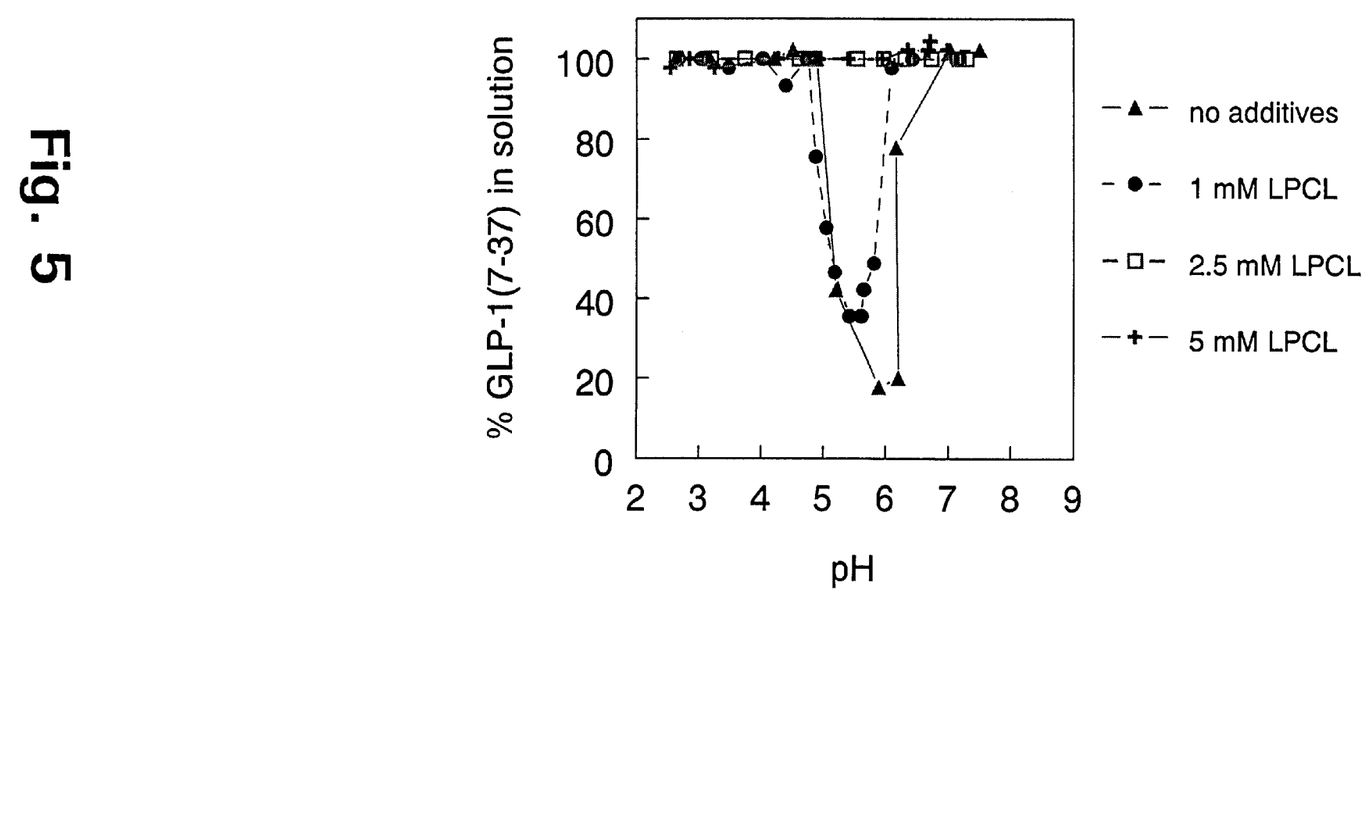

Equilibrium solubility was determined as a function of pH for 2 mg/ml solutions of GLP-1 (7–37) in the absence of additives and in the presence of increasing amounts of the detergent LPCL (lauroyl lysophosphatidyl choline). The results are shown in FIG. 5. For solutions containing 2.5 and 5 mM LPCL, 100% solubility was observed throughout the entire pH range. 1.0 mM LPCL did not provide the full effect, although solubility was significantly enhanced relative to the reference composition without the detergent.

Example 6

Figure 6:
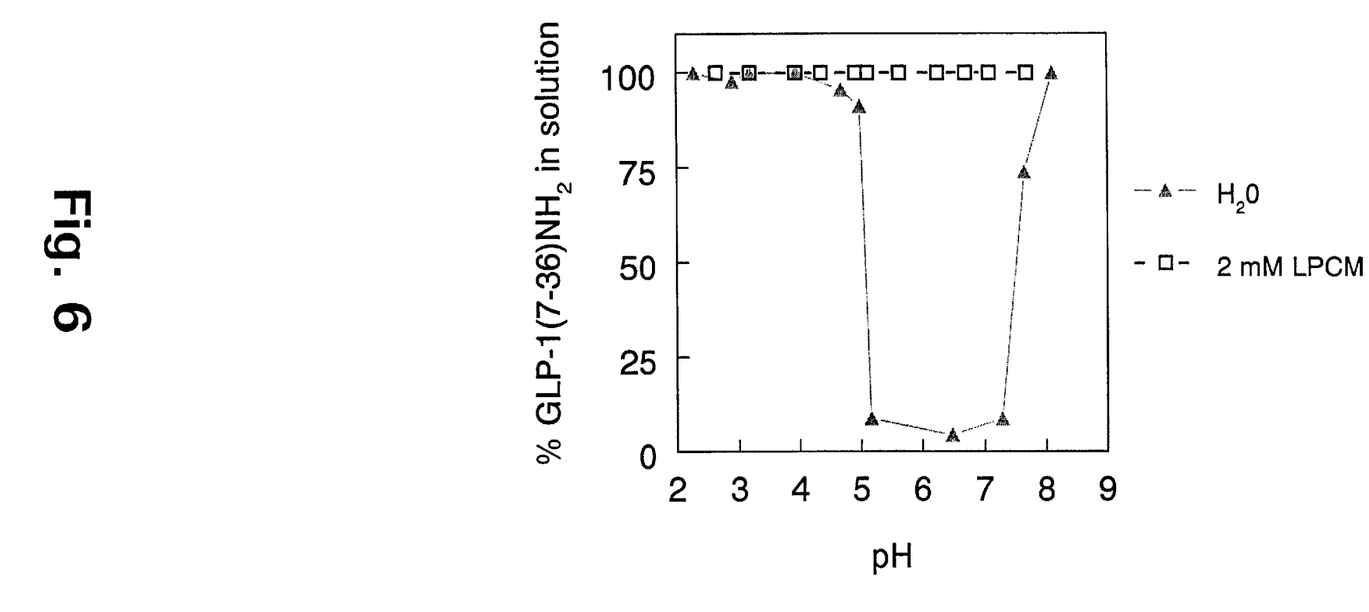

Equilibrium solubility was determined as a function of pH for 2 mg/ml solutions of GLP-1 (7–36)-NH$_2$ in the absence of additives and in the presence of increasing amounts of the detergent LPCM (myristoyl lysophosphatidyl choline). The results shown in FIG. 6 illustrate that 2 mM LPCM provides full solubility in comparison with the reference composition.

Example 7

Figure 7:
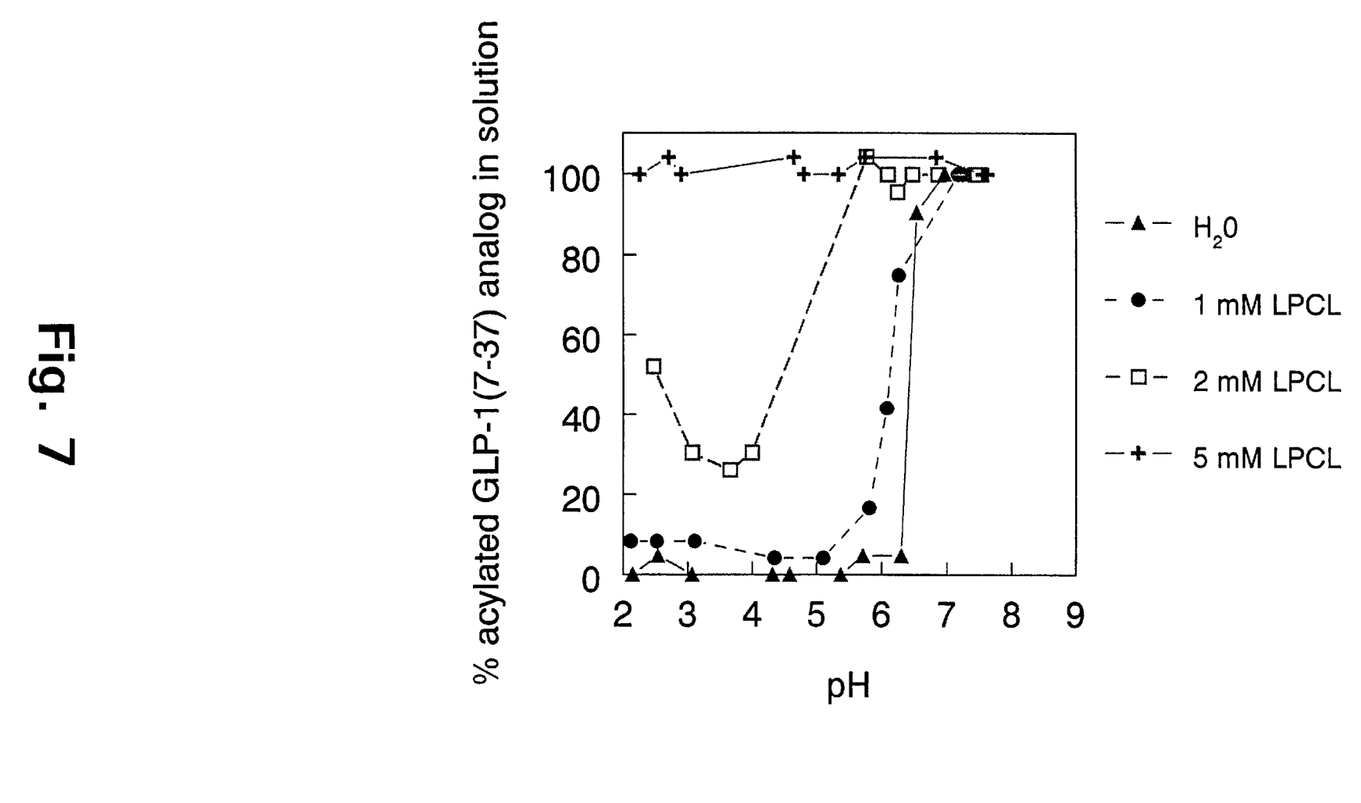

Equilibrium solubility was determined as a function of pH for 1 mg/ml solutions of the acylated GLP-1 (7–37) analogue N$^\epsilon$-hexadecanoyl-γ-glutamyl-Lys26,Arg34-GLP-1 (7–37) in the absence of additives and in the presence of increasing amounts of the detergent LPCL (lauroyl lysophosphatidyl choline). The results illustrated in FIG. 7 show that 1 mM and 2 mM LPCL enhance solubility relative to the reference composition, while full solubility is obtained in the presence of 5 mM LPCL.

What is claimed is:

1. A stabilized aqueous composition comprising at least one peptide selected from the group consisting of glucagon, glucagon-like peptide-1 (GLP-1), and analogues and derivatives thereof, together with a stabilizing and solubilizing amount of at least one detergent, wherein the detergent has at least 2 positive charges, at least 2 negative charges, or a combination of at least one positive charge and at least one negative charge, the peptide being present in a concentration of about 0.1–10 mg/ml, with the proviso that the detergent is not dodecyl phosphocholine, and wherein a stabilizing and solubilizing detergent is selected from the group consisting of (i) a 1-acyl-sn-glycero-3-phosphate ester of ethanolamine, choline, serine or threonine; and (ii) lauroyl lysophosphotidylcholine or myristoyl lysophosphatidylcholine.

2. The composition of claim 1 comprising about 0.5–2.5 mg of peptide per ml and about 1–5 mM of lauroyl or myristoyl lysophosphatidylcholine.

3. The composition of claim 1, further comprising at least one compound selected from the group consisting of an isotonic agent, a buffer substance buffering at pH 4–8, and a preservative.

4. The composition of claim 1, wherein the peptide is present in a concentration of about 0.2–5 mg/ml.

5. The composition of claim 4, wherein the peptide is present in a concentration of about 0.5–3 mg/ml.

6. The composition of claim 1, wherein the detergent is present in an amount of about 0.3–40 moles of detergent per mole of peptide.

7. The composition of claim 6, wherein the detergent is present in an amount of about 0.5–30 moles of detergent per mole of peptide.

8. The composition of claim 7, wherein the detergent is present in an amount of about 1–20 moles of detergent per mole of peptide.

9. A method for stabilizing an aqueous composition comprising at least one peptide selected from the group consisting of glucagon, glucagon-like peptide -1 (GLP-1), and analogues and derivatives thereof, wherein the peptide is present in a concentration of at least about 0.1 mg/ml, the method comprising adding to said composition a stabilizing and solubilizing amount of at least one detergent, wherein the detergent has at least 2 positive charges, at least 2 negative charges, or a combination of at least one positive charge and at least one negative charge, with the proviso that the detergent is not dodecyl phosphocholine, wherein the at least one peptide is stabilized in the aqueous composition, and wherein the detergent is selected from the group consisting of (i) a 1-acyl-sn-glycero-3-phosphate ester of ethanolamine, choline, serine or threonine and (ii) lauroyl lysophosphotidylcholine or myristoyl lysophosphatidylcholine.

* * * * *